United States Patent [19]
Moschel et al.

[11] Patent Number: 6,060,458
[45] Date of Patent: May 9, 2000

[54] OLIGODEOXYRIBONUCLEOTIDES COMPRISING $O^6$-BENZYLGUANINE AND THEIR USE

[75] Inventors: Robert C. Moschel; Gary T. Pauly, both of Frederick, Md.; Anthony E. Pegg, Hershey, Pa.; M. Eileen Dolan, Oak Park, Ill.

[73] Assignees: The United States of America as represented by the Department of Health and Human Services, Washington, D.C.; The Penn State Research Foundation, University Park, Pa.; Arch Development Corporation, Chicago, Ill.

[21] Appl. No.: 09/023,726

[22] Filed: Feb. 13, 1998

[51] Int. Cl.$^7$ .......................... A61K 31/70; C07H 21/04; C12N 5/06

[52] U.S. Cl. ........................... 514/44; 435/375; 536/23.1

[58] Field of Search ................................. 435/6, 15, 193, 435/366, 375; 514/44, 45; 536/23.1, 24.3, 24.31, 24.32, 24.33, 24.5, 25.3, 25.32, 27.81

[56] References Cited

U.S. PATENT DOCUMENTS

| | | | |
|---|---|---|---|
| 4,199,574 | 4/1980 | Schaeffer | 514/81 |
| 4,495,190 | 1/1985 | Hagberg et al. | 514/262 |
| 4,751,221 | 6/1988 | Watanabe et al. | 514/46 |
| 4,801,710 | 1/1989 | MacCoss et al. | 544/244 |
| 4,965,270 | 10/1990 | Harnden et al. | 514/262 |
| 5,075,445 | 12/1991 | Jarvest et al. | 544/276 |
| 5,091,430 | 2/1992 | Moschel et al. | 514/262 |
| 5,352,669 | 10/1994 | Moschel et al. | 514/45 |
| 5,358,952 | 10/1994 | Moschel et al. | 514/262 |
| 5,364,904 | 11/1994 | Farmer et al. | 524/832 |
| 5,525,606 | 6/1996 | Moschel et al. | 514/262 |
| 5,691,307 | 11/1997 | Moschel et al. | 514/262 |

FOREIGN PATENT DOCUMENTS

| | | |
|---|---|---|
| 184473 | 8/1986 | European Pat. Off. . |
| 335355 | 10/1989 | European Pat. Off. . |
| WO 91/13898 | 9/1991 | WIPO . |
| WO 94/29312 | 12/1994 | WIPO . |
| WO 96/04281 | 2/1996 | WIPO . |

OTHER PUBLICATIONS

Gerwitz et al. Facilitating oligonucleotide delivery: Helping antisense deliver on its promise. Proc. Natl. Acad. Sci. USA 93: 3161–3163, Apr. 1996.
Gura. Antisense has growing pains. Science 270: 575–577, Oct. 1995.
Rojanasakul. Antisense oligonucleotide therapeutics: Drug delivery and targeting. Adv. Drug. Delivery Rev. 18: 115–131, 1996.
Stull et al. Antigene, ribozyme, and aptamer nucleic acid drugs: Progress and prospects. Pharm. Res. 12: 465–483, Apr. 1995.
American Chemical Society, *Chemical Abstracts Service Registry Handbook*, Number Section 1965–1971, 11267R, col. 3, Registry No. 30360–74–8 (1965–71).
Beaman et al., in Zorbach and Tipson, *Synthetic Procedures in Nucleic Acid Chemistry*, 1, 41–43 (John Wiley & Sons, New York, NY 1968).
Beecham Group, "Preparation of Guaninie Derivatives and Their Use in Antiviral Preparations," *28–Heterocyles*, 103:123509a (1985).
Bisacchi et al., Preparation of [1β–(1α,2β,3α)]–2–amino–9–[2,3–bis(hydroxymethyl)cyclobutyl]–6H–purin–6–one, *Chem. Abs.*, 115:159683q (1991).
Bisacchi et al., Synthesis and Antiviral Activity of Enantiomeric Forms of Cyclobutyl Nucleoside Analogues, *J. Med. Chem.*, 34, 1415–1421 (1991).
Boon et al., *J. Chem. Soc.*, 96–102 (1951).
Bowles et al., "Synthesis and Antitumor Activity 9–(Tetrahydro–2–furyl)purine Analogs of Biologically Important Deoxynucleosides," *J. Med. Chem.* 6, 471–480 (1963).
Brix et al., "Androgen–linked Alkylating Agents: Biological Activity in MethylInitrosourea–induced Rat Mammary Carcinoma," *J. Cancer Res. Clinical Oncology*, 116, 538–549 (1990).
Carbon et al., "Synthesis and Reactions of 5–Bromomethyl– and 5–Chloromethyluracil," *J. Org. Chem.*, 25, 1731–1734 (1960).
Chae et al., *J. Med. Chem.*, 37 (3), 342–347 (1994).
Chae et al., *J. Med. Chem.*, 38 (2), 359–365 (1995).
Christian et al., "Promising New Agents Under Development by the Division of Cancer Treatment, Diagnosis, and Centers of the National Cancer Institute," *Seminars in Oncology*, 24(2), 219–240 (1997).
Ciocco et al., "Specific Labeling of $O^6$–Alkylguanine–DNA Alkyltransferase by Reaction with $O^6$–(p–Hydroxy[$^3$H]Methylbenzyl)guanine," *Cancer Research*, 55, 4085–4091 (1995).

(List continued on next page.)

*Primary Examiner*—George C. Elliott
*Assistant Examiner*—Thomas G Larson
*Attorney, Agent, or Firm*—Leydig, Voit & Mayer, Ltd.

[57] ABSTRACT

The present invention provides a single-stranded oligodeoxyribonucleotide, which (i) comprises from about 5 to 11 bases, at least one of which is a substituted or an unsubstituted $O^6$-benzylguanine, and (ii) inactivates human AGT. The present invention also provides a single-stranded oligodeoxyribonucleotide, which can inactivate a mutant human AGT, which either is not inactivated by $O^6$-benzylguanine or is less inactivated by $O^6$-benzylguanine than by said single-stranded oligodeoxyribonucleotide. A phosphate of the single-stranded oligodeoxyribonucleotide can be replaced by a methylphosphonate or a phosphorothioate. The present invention also provides a composition comprising such an oligodeoxyribonucleotide. In addition, the present invention provides a method of enhancing the effect of an antineoplastic alkylating agent, which alkylates the $O^6$ position of guanine residues in DNA, in the chemotherapeutic treatment of cancer in a mammal, which method comprises the co-administration to the mammal of a cancer-treatment effective amount of an antineoplastic alkylating agent and a chemotherapeutic treatment-enhancing amount of a present inventive oligodeoxyribonucleotide or composition thereof.

61 Claims, 2 Drawing Sheets

OTHER PUBLICATIONS

Crone et al., *Cancer Res.*, 53, 4750–4753 (1993).
Crone et al., "Mutations in Human $O^6$–Alkylguanine–DNA Alkyltransferase Imparting Resistance to $O^6$–Benzylguanine," *Cancer Research*, 54, 6221–6227 (1994).
Crone et al., "Mutations in the Ada $O^6$–Alkylguanine–DNA Alkyltransferase Conferring Sensitivity to Inctivation by $O^6$Benzylguanine and 2,4–Diamino–6–Benzyloxy–5–Nitrosopyrimidine," *Carcinogenisis*, 16(8), 1687–1692 (1995).
Daves, Jr., et al., *J. Am. Chem. Soc.*, 82, 2633–2640 (1960).
Delia et al., *Heterocycles*, 20, 1805–1809 (1983).
Dolan et al., "Effect of $O^6$–Alkylguanine Pretreatment on the Sensitivity of Human Colon Tumor Cells to the Cytotoxic Effects of Chloroethylating Agents," *Cancer Research*, 46, 4500–4505 (1986).
Dolan et al., "Depletion of $O^6$–Alkylguanine–DNA Alkyltransferase Activity in Mammalian Tissues and Human Tumor Xenografts in Nude Mice by Treatment with $O^6$–Methylguanine," *Cancer Chemother. Pharmacol.*, 25, 103–108 (1989).
Dolan et al., *Cancer Commun.*, 2, 371–377 (1990).
Dolan et al., *Proc. Natl. Acad. Sci. U.S.A.*, 87, 5368–5372 (1990).
Dolan et al., *Cancer Res.*, 51, 3367–3372 (1991).
Dolan et al., "Comparison of the Inactivation of Mammalian and Bacterial $O^6$–Alkylguanine–DNA Alkyltransferases by $O^6$–Benzylguanine and $O^6$–Methylguanine," *Carcinogenesis*, 12 (12), 2305–2309 (1991).
Dolan et al., *Biochem. Pharmacol.*, 46, 285–290 (1993).
Dolan et al., *Cancer Chem. Pharmacol.*, 32, 221–225 (1993).
Dolan et al., "Metabolism of $O^6$–Benzylguanine, an Inactivator of $O^6$–Alkylguanine–DNA Alkyltransferase," *Cancer Research*, 54, 5123–5130 (1994).
Dolan et al., "$O^6$–Benzylguanine and Its Role in Chemotherapy," *Clinical Cancer Research*, 3, 837–847 (1997).
Door et al. in *Cancer Chemotherapy Handbook*, 715–742 (Elsevier Science Publishing, New York, NY 1980).
Edara et al., "Resistance of the Human $O^6$–Alkylguanine–DNA Alkyltransferase Containing Arginine at Coden 160 to Inactivation by $O^6$–Benzylguanine," *Cancer Research*, 56, 5571–5575 (1996).
Elder et al., "Differential Inactivation of Mammalian and *Escherichia coli* $O^6$–alkylguanine–DNA alkyltransferase by $O^6$–Benzylguanine," *Biochem.*, 298, 231–235 (1994).
Felker et al., *Cancer Chem. Pharmacol.*, 32, 471–476 (1993).
Fischer et al. in *Cancer Chemotherapy Handbook*, 3rd ed., 4–9, 60–61, 164–165, 171 (Year Book Medical Publishers, Inc., Chicago, IL 1989).
Folkman et al., "A New One–Step Method for the Preparation of 3',5'–Bisphosphates of Acid–Labile Deoxynucleosides," *Chem. Res. Toxicol.*, 3, 536–539 (1990).
Fondy et al., "Haloacetamido Analogues of 2–Amino–2–deoxy–D–glucose and 2–Amino–2–deoxy–D–galactose. Syntheses and Effects on the Friend Murine Erythroleukemia," *J. Med. Chem.*, 21 (12), 1222–1225 (1978).

Ford et al., "A Simple Method for Predicting Hydration Energies of Organic Cations Derived from Protonation of Alkylation of Neutral Oxygen and Nitrogen Bases," *J. Org. Chem.*, 48, (13), 2226–2233 (1983).
Friedman et al., *J. Natl. Cancer Inst.*, 84, 1926–1931 (1992).
Frihart et al., "Allylic Rearrangement from $O^6$ to C–8 in the Guanine Series," *J. Am. Chem. Soc.*, 95 (21), 7174–7175 (1973).
Gerson et al., "Synergistic Efficacy of $O^6$–Benzylguanine and 1,3–Bis(2–Chloroethyl–Nitrosourea (BCNU) in a Human Colon Cancer Xenograft Completely Resistant to BCNU Alone," *Biochem. Pharmacol.*, 45 (2), 483–491 (1993).
Gerson et al., "Drug Resistance Mediated by DNA Repair: The Paradigm of $O^6$–Alkylguanine DNA Alkyltransferase," Proceedings of The American association for Cancer Research, 35, 699–700 (1994).
Gerster et al., *J. Am. Chem. Soc.*, 87, 3752–3759 (1965).
Goodtzova et al., "Activation of Human $O^6$–Alkylguanine–DNA Alkyltransferase by DNA," *Biochemistry*, 33(28), 8385–8390 (1994).
Goodtzova et al., "Repair of $O^6$–Benzylguanine by the *Escherichia coli* Ada and Ogt and the Human $O^6$–Alkylguanine–DNA Alkyltransferase," *The Journal of Biological Chemistry*, 272(13), 8332–8339 (1997.
Green et al., "Preparation of Purine Acyclonucleoside Intermediates," *Chem. Abs.*, 115:28993t (1991).
Hagberg et al., "Guanine Derivatives," *33–Carbohydrates*, 97:182809d (1982).
Hannah et al., "Substituted Butylguanines and Their Utilization in Antiviral Compositions," *26–Biomolecules*, 104:68682 (1986).
Hannah et al., "Carba–acylonucleoside Antiherpetic Agents," *J. Heterocyclic Chem.*, 26, 1261–1271 (1989).
Harnden et al., "Synthesis and Antiviral Activity of 9–[4–Hydroxy–3–(hydroxymethyl)but–1–yl]purines," *J. Med. Chem.*, 30, 1636–1642 (1987).
Harnden et al., "Prodrugs of the Selective Antiherpesvirus Agent 9–[4–Hydroxy–3–(hydroxymethyl)but–1–yl]guanine (BRL 39123) with Improved Gastrointestinal Absorption Properties," *J. Med. Chem.*, 32, 1738–1743 (1989).
*Harrison's Principles of Internal Medicine*, 10th ed., 751, 758, 766–775 (1983).
Himmelsback et al., "The p–Nitrophenylethyl (NPE) Group. A Versatile New Blocking Group for Phosphate and Aglycone Protection in Nucleosides and Nucleotides," *Tet.*, 40 (1), 59–72 (1984).
Holmes et al., "Rearrangement of Cinnamyl Groups from $O^6$ to C–8 in the Guanine Series," *J. Org. Chem.*, 43 (3), 516–518 (1978).
House in *Modern Synthetic Reactions*, 2nd ed., 536–541, 602–603 (1972).
Jacobs et al., "Synthesis of SQ–32,829, A New Nucleoside Antiviral Agent," *Tet. Letters*, 30 (50), 6955–6958 (1989).
Jones et al., *J. Am. Chem. Soc.*, 82, 3773–3779 (1960).
Kanugula et al., "Alteration of Arginine–128 to Alanine Abolishes the Ability of Human $O^6$–Alkylguanine–DNA Alkyltransferase to Repair Methylated DNA but Has No Effect on Its Reaction with $O^6$–Benzylguanine," *Biochemistry*, 34, 7113–7119 (1995).
Karkas et al., "Enzymatic Phosphorylation of the Antiherpetic Agent 9–[2,3–Dihydroxy–1–propoxy)methyl]guanine," *J. Med. Chem.*, 29 (5), 842–848 (1986).
Kempter et al., *Chemical Abstract* 72: 100650 (1970).

Kim et al., "Acyclic Purine Phosphonate Analogues as Antiviral Agents. Syntheisis and Structure–Activity Relationships," *J. Med. Chem.,* 33, 1207–1213 (1990).

Kjellberg et al., "Regioselective Alkylation of 6–(8–Methoxyethoxy) Guanine to Give the 9–Alkylguanine Derivative," *Tet. Letters,* 27 (7), 877–880 (1986).

Kosary et al., *Acta Pharm. Hung.,* 49, 241–247 (Chemical Abstract 112: 216531) (1989).

Kusmiesek et al., "Synthesis of $N^2$,3–Ethenodeoxyguanosine,$N^2$,3–Ethenodeoxyguanosine 5'–Phosphate, and $N^2$,3–Ethenodeoxyguanosine 5'–Triphosphate. Stability of the Glycosyl Bond in the Monomer and in Poly(dG, εdG–dC)," *Chem. Res. Toxicol.,* 2, 230–233 (1989).

Leonard et al., "Intramolecular Mechanism of the Allylic Rearrangement from $O^6$ to C–8 in the Guanine Series Double Labeling Experiments," *J. Am. Chem. Soc.,* 96, 5894–5903 (1974).

MacCoss et al., "Synthesis of the Chiral Acyclonucleoside Antiherpetic Agent (S)–9–(2,3–Dihydroxy–1–Propoxymethyl)guanine," *Tet. Letters,* 26 (15), 1815–1818 (1985).

MacCoss et al., "Regioselective Synthesis of 9–Substituted Purine Acyclonucleoside Derivatives," *33–Carbohydrates,* 105:115383f (1986).

Mansuri et al., "Preparation of 4–phosphoromethoxycyclopent(en)–1–ylpurines and –pyrimidines as Virucides, Bactericides, and Neoplasm Inhibitors," *Chem. Abs.,* 113:152983n (1990).

March, in *Advanced Organic Chemistry,* 3rd ed., 358–359, 574–575, 802–803, 982–985 (John Wiley & Sons 1985).

Marcus–Sekura et al., "Comparative Inhibition of Chloramphenicol Acetyltransferase Gene Expression by Antisense Oligonucleotide analogues Having alkyl Phosphotriester, methylphosphonate and phosphorothioate Linkages," *Nucleic acids Research,* 15(14), 5749–5763 (1987).

Margison et al., "Resistance to Alkylating Agents: More or Less," *Anti–Cancer Drugs,* 7(Suppl. 3), 109–116 (1996).

Milne et al., "Synthesis and Antitumor Activity of α– and β–2'–Deoxy–6–selenoguanosine and Certain Related Derivatives," *J. Med. Chem.,* 17 (3), 263–268 (1974).

Mitchell et al., *Cancer Res.,* 52, 1171–1175 (1992).

Moschel et al., "Sustituted–Induced Effects on the Stability of Benzylated Guanosines: Model Systems for the Factors Influencing the Stability of Carcinogen–Modified Nucleic Acids," *J. Org. Chem.,* 49 (2), 363–372 (1984).

Moschel et al., *J. Org. Chem.,* 51, 4180–4185 (1986).

Moschel et al., "Reactivity Effects on Site Selectivity in Nucleoside Aralkylation: A Model for the Factors Influencing the Sites of Carcinogen–Nucleic Acid Interactions," *33–Carbohydrates,* 107:115902r (1989).

Moschel et al., *J. Med. Chem.,* 35 (23), 4486–4491 (1992).

Murray, "Dioxiranes," *Chem. Rev.,* 89 (5), 1187–1201 (1989).

O'Brien et al., *J. Med. Chem.,* 9, 573–575 (1966).

Pansare et al., "Synthesis of N–Protected α–Amino Acids from N–(Benzyloxycarbonyl)–L–Serine Via Its β–Lactone: $N^\alpha$–(Benzyloxycorbonyl)–β–(Pyrazol–1–yl)–L–Alanine," *Organic Syntheses,* 70 (1), 1–9 (1992).

Pansare et al., "Synthesis of N–tert–Butoxycarbonyl–L–Serine β–Lactone and the p–Toluenesulfonic Acid Salt of (S)–3–Amino–2–Oxetanone," *Organic Syntheses,* 70, 10–17 (1992).

Pauly et al., "Synthesis and Properties of H–ras DNA Sequences Containing $O^6$–Substituted 2'–Deoxyguanosine Residues at the First, Second, or Both Positions of Codon 12," *Chem. Res. In Toxic.,* 1 (6), 391–397 (1988).

Pauly et al., "A Sectored Colony Assay for Monitoring Mutagenesis by Specific Carcinogen–DNA Adducts in *Escherichia coli,*" *Biochemistry,* 30 (50), 11700–11706 (1991).

Pegg et al., "Use of Antibodies to Human $O^6$Alkylguanine–DNA Alkyltransferase to Study the Content of This Protein in Cells Treated with $O^6$–Benzylguanine or N–Methyl–N'–Nitro–N–Nitrosoguanidine," *Carcinogenesis,* 12 (9), 1679–1683 (1991).

Pegg et al., "Inhibition of $O^6$Alkylguanine–DNA Alkyltransferase as a Means to Enhance the Effectiveness of Chemotherapeutic Alkylating Agents," Proceedings of The American association for Cancer Research, 34, 565 (1993).

Pegg et al., "Mechanism of Inactivation of Human $O^6$Alkylguanine–DNA Alkyltransferase by $O_6$–Benzylguanine," *Biochemistry,* 32, 11998–12006 (1993).

Pegg et al., "Structure, Function, and Inhibition of $O^6$Alkylguanine–DNA Alkyltransferase," *Progress in Nucleic Acid Research and Molecular Biology,* 51, 167–223 (1995).

Pegg, "Mammalian $O^6$Alkylguanine–DNA Alkyltransferase: Regulation and Importance in Response to Alkylating Carcinogenic and Therapeutic Agents," *Cancer Res.,* 50, 6119–6129 (1990).

Pfleiderer et al., *Chem. Ber.,* 94, 12–18 (1961).

Pfleiderer et al., *Liebigs Ann. Chem.,* 726, 201–215 (1969).

Philips et al., *J. Org. Chem.,* 28, 1488–1490 (1963).

Poe et al., *Chemical Abstract* 107: 194511 (1987).

Ram et al., *Chem. Abstr.,* 101 (25), 230466q (1984).

Ramzaera et al, "Alkalation of 6–methylthio– and 6–benzyloxyguanine under Phase–Transfer Conditions," *Synth. Commun.,* 19 (18), 3121–3128 (1989).

Rideout et al., "Perparation of (3'–azido–2',3'–dideozy ) Purine Nucleosides as Medical Antivirals," *Chem. Abs.,* 116:84108r (1992).

Robins et al., "Purine Nucleosides. XXIV. A New Method for the Synthesis of Guanine Nucleosides. Preparation of 2'–Deoxy–α– and –β–Guanosines and the Corresponding $N^2$–Methyl Derivatives," *34–Synthesis of Amino Acids, Peptides, and Proteins,* 71:39386w (1969).

Robins et al., *J. Org. Chem.,* 34 (7), 2160–2163 (1969).

Roy et al., "Pharmacokinetics and Metabolism in Rats of 2,3–Diamino–5–Benzyloxy–5–NitrosopyRimidine, an Inactivator of $O^6$Alkylguanin–DNA Alkyltransferase," *American Society for Pharmacology and Experimental Therapeutics,* 24(11), 1205–1211 (1996).

Schaffer et al., "Substituted Purine Derivatives," *Chem. Abs.,* 84:180300p (1976).

Schaffer et al., "Compositions for Treating Viral Infections and Guanine Acyclic Nucleosides," *Chem. Abs.,* 93:186414m (1980).

Shealey et al., *J. Org. Chem.,* 27, 4518–4523 (1962).

Skinner, Jr., "Potential Anticancer Agents XXVIII. Synthesis of 5–(Chloromethyl)uracil," *Org. Chem.,* 25, 149–151 (1960).

Slusarchyk et al., "Synthesis of SQ–33,054, A Novel Cyclobutane Nucleoside with Potent Antiviral Activity," *Tet. Letters,* 30 (47), 6453–6456 (1989).

Slusarchyk et al., "Preparation of [bis(hydroxymethyl)cyclobutyl]Purines and –Pyrimidines as Virucides," *Chem. Abs.*, 112:179713r (1990).

Slusarchyk et al., "Preparation of 7-[3-(hydroxymethyl)cyclobutyl]Purines and –Pyrimidines as Antiviral Agents," *Chem. Abs.*, 113:40344y (1990).

Stein et al., "Inhibition of Human Purine Nucleoside Phosphorylase by Acyclic Nucleosides and Nucleotides," *Biochem Pharmacol.*, 36(8), 1237–1244 (1989).

Terashima et al., "Substrate Specificity of Human $O^6$–Methylguanine–DNA Methyltransferase for $O^6$–Benzylguanine Derivatives in Oligodeoxynucleotides," *Chem. Res. Toxicol.*, 10, 1234–1239 (1997).

Tisdale et al., "Preparation of 2'–Deoxy–2'–Fluororibonucleosides as Medicinal Virucides," *Chem. Abs.*, 115:230514t (1991).

Tolman et al., "4–(Guanin–9–yl)Butanals and Antiviral Compositions Containing Them," *Chem. Abs.*, 105:114840r (1986).

Tolman et al., "9–[2–(Hydroxymethyl)cycloalkylmethyl] Guanines as Antiviral Agents and Their Preparation," *26–Biomolecules*, 110:212501d (1989).

Tondeur et al., "Fast Atom Bombardment and Collisional Activation Mass Spectrometry as Probes for the Identification of Positional Isomers in a Series of Benzylated Guanosines," *Chem. Abs.*, 104:199241y (1986).

Trichtinger et al., "Synthesis of $O^6$–p–Nitrophenylethyl Guansoine and 2'–Deoxyguanosine Derivatives," *Tet. Letter*, 24 (7), 711–714 (1983).

Vemishetti et al., "Synthesis of Chiral 1',2'–Seco–Nucleosides of Guanine and Uracil," *Nucleosides and Nucleotides*, 8 (2), 201–211 (1989).

Vemishetti et al., "The Preparation of 2'–Deoxy–2'–Fluoro–1',2'–Seconucleosides as Potential Antiviral Agents," *J. Med. Chem.*, 33, 681–686 (1990).

Wakabayashi et al., *Nippon Dojo–Hiryyogaku Zasshi*, 41, 193–200 (1970). (Abstract CA73: 108869m).

Wallace, Raymond, "Hydroxylamine–O–sulfonic Acid—A Versatile Synthetic Reagent," *Aldrichimia Acta*, 13, 3–11 (1980).

Wasserman et al., *Cancer*, 36, 1258–1268 (abstract) (1975).

Webb et al., "Antiviral Phosphonomethoxyalkylpurines and – pyrimidines and their Preparation," *26–Biomolecules*, 109:190136 (1988).

Webb et al., "Preparation of [(Purin–9–yl)alkoxy)methyl] Phosphonic Acids as Antiviral Agents," *Chem. Abs.*, 111:39105y (1989).

Wilson, "Synthetic Approaches to a Carboranyl Thiouracil," *Pigment Cell Research*, 2, 297–303 (1989).

Winograd et al., "Human Tumor Xenografts in the Nude Mouse and their Value as Test Models in Anticancer Drug Development (Review)," *In Vivo*, 1, 1–14 (1987).

Yu et al., "Preparation of Chiral 2–(Phosphonomethoxy)Propylguanines as Antiviral Agents," *Chem. Abs.*, 116:41987j (1992).

Zahler et al., "Preparation of Purinyl– and Pyrimidinyl–Cyclobutanes as Antiviral Agents," *Chem.Abs.*, 112:158265f (1990).

Zahler et al., Purinyl– and Pyrimidinylcyclobutanes and Their Use as Antiviral Agents, *Chem.Abs.*, 113:152981k (1990).

Zahler et al., "Preparation of Virucidal Purinly– and Pyrimidinyl–Tetrahydrofurans," *33–Carbohydrates*, 114:122985t (1991).

Zahler et al., "Preparation of 4,5–Bis(hydroxymethyl)Tetrahydrofuran–3–yl–Purines and Pyrimidines as Virucides," *33–Carbohydrates*, 116:84113p (1991).

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (synthetic)

(iii) HYPOTHETICAL: NO (iv) ANTI-SENSE: NO (ix) FEATURE:
        (A) NAME/KEY: misc_feature
        (B) LOCATION: 6
        (D) OTHER INFORMATION: The guanine at position 6 is
            O6-benzylguanine (xi) SEQUENCE DESCRIPTION: SEQ ID NO:1:

TGTGAGCTGT G                                                  11

OLIGODEOXYRIBONUCLEOTIDES COMPRISING O$^6$-BENZYLGUANINE AND THEIR USE

TECHNICAL FIELD OF THE INVENTION

This invention relates to oligodeoxyribonucleotides comprising O$^6$-benzylguanine and related compositions. This invention also relates to the use of such oligodeoxyribonucleotides and related compositions to enhance the effect of an antineoplastic alkylating agent in the chemotherapeutic treatment of cancer in a mammal.

BACKGROUND OF THE INVENTION

O$^6$-alkylguanine-DNA alkyltransferase (AGT) is a DNA repair protein. AGT removes alkyl and aralkyl groups that become attached at the O$^6$ position of guanine in DNA or alkyl groups at the O$^4$ position of thymine in DNA following exposure to mutagenic and/or carcinogenic alkylating agents. It does so by bringing about a stoichiometric transfer of the group attached to the O$^6$ position of a guanine residue in DNA, for example, to a cysteine residue within the AGT protein (Pegg, *Cancer Research* 50: 6119–6129 (1990)). Accordingly, AGT is beneficial to a normal cell because it removes the adducts that are formed in DNA by toxic, mutagenic and carcinogenic agents, thereby restoring the DNA to its original state and helping to prevent DNA mutations that can lead to initiation of tumor formation. Unfortunately, AGT is also beneficial to a cancerous cell because it also removes those adducts that are formed at the O$^6$ position of guanine in DNA by antineoplastic alkylating agents, such as monofunctional methylating agents, e.g., procarbazine, dacarbazine and temozolomide, and chloroethylating agents, i.e., CENUs, such as BCNU, ACNU, CCNU, MeCCNU, fotemustine and clomesone (Pegg et al., *Prog. Nucleic Acid Research Molec. Biol.* 51: 167–223 (1995)). The resulting alkylated AGT molecule is consequently inactivated and is unable to carry out subsequent dealkylation reactions. The presence of more AGT in a cell increases its capacity to repair DNA by this mechanism compared to a cell that has less AGT.

The reduction in the efficacy of cancer chemotherapeutic drugs due to AGT, which acts without requiring the presence of additional enzymes or cofactors, and the existence of a high correlation between AGT activity and reduction in sensitivity of tumor cells to nitrosoureas have led to AGT becoming a prime target for modulation. Modulation has been attempted by two different routes. One route is indirect and involves the use of methylating agents that introduce O$^6$-methylguanine lesions into DNA for subsequent repair by AGT, thereby depleting levels of AGT. The other route is direct and involves the use of an inactivator of AGT, such as an O$^6$-aralkylguanine (see, for example, Moschel et al., U.S. Pat. Nos. 5,091,430, 5,352,669 and 5,358,952).

The first O$^6$-alkylguanine developed as a potential inactivator of AGT was O$^6$-methylguanine. Although initial results obtained in cell culture appeared promising, O$^6$-methylguanine was only able to reduce AGT activity by 85% and was not able to enhance the therapeutic index of BCNU in the treatment of mice carrying human tumor xenografts (Pegg et al. (1995), supra). In addition, the use of O$^6$-methylguanine was plagued with problems, such as poor solubility, poor affinity for AGT, poor uptake into cells, and lack of selectivity, which necessitated high dosages of O$^6$-methylguanine to be administered for long periods of time (Pegg et al. (1995), supra).

The testing of O$^6$-methylguanine led to the development of O$^6$-benzylguanine as a potential inactivator of AGT (Moschel et al., *J. Med. Chem.* 35(23): 4486–4491 (1992); Pegg et al., *Biochem.* 32(45): 11998–12006 (1993); Pegg et al., *Proc. Amer. Assoc. Cancer Research* 34: 565 (1993); and Gerson et al., *Proc. Amer. Assoc. Cancer Research* 35: 699 (1994)). O$^6$-benzylguanine has been shown to inactivate AGT in Mer$^{30}$ cells, thereby rendering them more sensitive to the cytotoxic effects of alkylating agents (Pegg et al. (1995), supra). Furthermore, the correlation between the degree of increased sensitivity to alkylating agents and the level of inhibition of AGT activity by O$^6$-benzylguanine is strong (Pegg et al. (1995), supra). O$^6$-benzylguanine also has been shown to increase the sensitivity of oxic and hypoxic brain tumor cells to BCNU (Pegg et al. (1995), supra). Increased sensitivity to MeCCNU or BCNU due to the prior administration of O$^6$-benzylguanine also was demonstrated in nude mice carrying SF767 tumor xenografts (Dolan et al., *Cancer Comm.* 2(11): 371–377 (1990)), mice carrying a D341MED or a D456MG brain tumor xenograft or a TE-671 human rhabdosarcoma xenograft (Pegg et al. (1995), supra; Friedman et al., *J. Natl. Cancer Inst.* 84(24): 1926–1931 (1992); and Felker et al., Cancer Chemother. Pharmacol. 32: 471–476 (1993)). A significant increase in median survival in animals treated with O$^6$-benzylguanine prior to BCNU compared to BCNU alone was demonstrated in the intracranial D341 MED medulloblastoma model (Pegg et al. (1995), supra; and Friedman et al. (1992), supra). Similar observations have been made with respect to colon tumor xenografts having high AGT activity (Mitchell et al., *Cancer Research* 52: 1171–1175 (1992); and Dolan et al., *Biochem. Pharmacol.* 46(2): 285–290 (1993)) and the Dunning rat prostate tumor model (Pegg et al. (1995), supra; and Dolan et al., *Cancer Chemother. Pharmacol.* 32: 221–225 (1993)). Exogenously added DNA, such as single-stranded and double-stranded oligodeoxyribonucleotides ranging in length from 4 to 16 bases (or base pairs), in particular 12-base (or 12-base pair) oligodeoxyribonucleotides, have been shown to stimulate the production of guanine by recombinant human AGT from O$^6$-benzylguanine, but not 9-substituted O$^6$-benzylguanines (Goodtzova et al., *Biochem.* 33(28): 8385–8390 (1994)).

p-Chlorobenzyl and p-methylbenzyl analogues of O$^6$-benzylguanine also have been shown to inactivate AGT rapidly and irreversibly (Dolan et al., *PNAS USA* 87: 5368–5372 (1990); and Dolan et al., *Cancer Research* 51: 3367–3372 (1991)). Such analogues have been shown to be as good as O$^6$-benzylguanine in enhancing the cytotoxicity of chloroethylating agents toward SF767 glioma cells and HT29 colon tumor cells (Dolan et al. (1990), supra; and Dolan et al. (1991), supra). Based on such results, O$^6$-benzylguanine was suggested to be potentially useful in the treatment of mer+ tumors as an adjuvant to an alkylating agent that produces a toxic lesion at the O$^6$ position of guanine residues in DNA (Dolan et al. (1991), supra).

O$^6$-benzylguanine, in combination with BCNU, is now in clinical trials. Although O$^6$-benzylguanine is clearly the most promising compound for inactivating AGT at this time, it is not an ideal drug. It has only limited solubility in water and is characterized by rapid clearance from blood plasma due to metabolic conversion to other compounds (Dolan et al., *Cancer Research* 54: 5123–5130 (1994)).

Furthermore, in vitro data suggest that O$^6$-benzylguanine may not be able to inactivate mutant forms of AGT, which could result from mutations induced by chemotherapeutic drugs, such as chloroethylating or methylating agents, in vivo. Given that the *E. coli* Ada-C protein and Ogt alkyltransferase and the yeast AGT are insensitive to O$^6$-benzylguanine (Pegg et al., *Biochem.* 32: 11998–12006

(1993); and Elder et al., *Biochem. J.* 298: 231–235 (1994)), site-directed mutagenesis (Crone et al., Cancer Research 53: 4750–4753 (1993); Crone et al., *Cancer Research* 54: 6221–6227 (1994); and Edara et al., *Cancer Research* 56: 5571–5575 (1996)) has been used to create mutant AGTs, which differ from the wild-type AGT by one or more amino acid changes. Several mutant AGTs have been found to be much less sensitive than wild-type AGT to inactivation by $O^6$-benzylguanine (Crone et al. (1993), supra; Crone et al. (1994), supra; and Edara et al. (1996), supra).

In an effort to address its limited solubility in water, $O^6$-benzylguanine has been formulated in a polyethylene glycol-400-based vehicle (Pegg et al. (1995), supra). The formulation has been shown to be effective in sensitizing D456MG glioblastoma xenografts in nude mice to BCNU at lower doses than earlier cremophor-EL-based formulations (Pegg et al. (1995), supra). significantly more effective than $O^6$-benzylguanine at inactivating AGT in human HT29 colon tumor cell extracts and intact HT29 colon tumor cells (Chae et al., *J Med Chem*. 38: 359–365 (1995)). Consequently, it has been suggested that these new compounds may be superior to $O^6$-benzylguanines as chemotherapeutic adjuvants for enhancing the effectiveness of antitumor drugs that modify the $O^6$-position of guanine residues in DNA (Chae et al. (1995), supra). However, some of the pyrimidines appear to be metabolized and rapidly excreted (Roy et al., *Drug Metab. Disposition*, 24: 1205–1211 (1996)).

Sixteen-base oligonucleotides comprising one or two $O^6$-methyl-, $O^6$-ethyl- or $O^6$-benzyl-2'-deoxyguanosine residue(s) have been generated. These have the sequences of the rat H-ras gene extending from codon 9 through the first base of codon 14. These oligonucleotides were used to establish whether the type of $O^6$-substituted 2'-deoxyguanosine residue or its position leads to any significant differential disruption of duplex stability or conformation that might ultimately contribute to a rationale for the apparent selective mutability of the second guanine residue of codon 12 of H-ras in rat mammary carcinomas upon activation following a single dose of NMU (Pauly et al., *Chem. Research Toxicol*. 1(6): 391–398 (1988)). Related sixteen-base oligonucleotides also have been incorporated into a cassette plasmid for use in *E. coli* to monitor the mutagenicity of carcinogen-modified bases in a simple sectored colony assay (Pauly et al., *Biochemistry* 30: 11700–11706 (1991)) and to compare their repair by mammalian and bacterial AGTs (Elder et al., *Biochem. J.* 298: 231–235 (1994)). An example of such a sixteen-base oligonucleotide was found to deplete AGT activity rapidly and has been described as a possibly good substrate for AGT (Dolan et al. (1990), supra).

In view of the above, there remains a need for an inhibitor of AGT, which (i) is more water-soluble than $O^6$-benzylguanine, (ii) is effective at a much lower concentration than $O^6$-benzylguanine, (iii) is capable of inactivating mutant forms of AGT, which are resistant to inactivation by $O^6$-benzylguanine, and (iv) is still more active than $O^6$-methylguanine and analogues thereof. Accordingly, it is an object of the present invention to provide such an inactivator. It is another object of the present invention to provide a composition comprising such an inactivator. It is yet another object of the present invention to provide a method of using such inactivators and compositions. These and other objects will become apparent from the detailed description set forth below.

BRIEF SUMMARY OF THE INVENTION

The present invention provides a single-stranded oligodeoxyribonucleotide, which (i) comprises from about 5 to 11 bases, at least one of which is a substituted or an unsubstituted $O^6$-benzylguanine, and (ii) inactivates human AGT. The present invention also provides a single-stranded oligodeoxyribonucleotide, which can inactivate a mutant human AGT, which either is not inactivated by $O^6$-benzylguanine or is less inactivated by $O^6$-benzylguanine than by said single-stranded oligodeoxyribonucleotide. One or more phosphates of the single-stranded oligodeoxyribonucleotide can be modified, e.g., by replacement with a methylphosphonate or a phosphorothioate. The present invention also provides a composition comprising such an oligodeoxyribonucleotide. In addition, the present invention provides a method of enhancing the effect of an antineoplastic alkylating agent, which alkylates the $O^6$ position of guanine residues in DNA, in the chemotherapeutic treatment of cancer in a mammal. The method comprises the co-administration to the mammal of a cancer-treatment effective amount of an antineoplastic alkylating agent and a chemotherapeutic treatment-enhancing amount of a present inventive oligodeoxyribonucleotide or a composition thereof.

DETAILED DESCRIPTION OF THE INVENTION

Figure 1A:
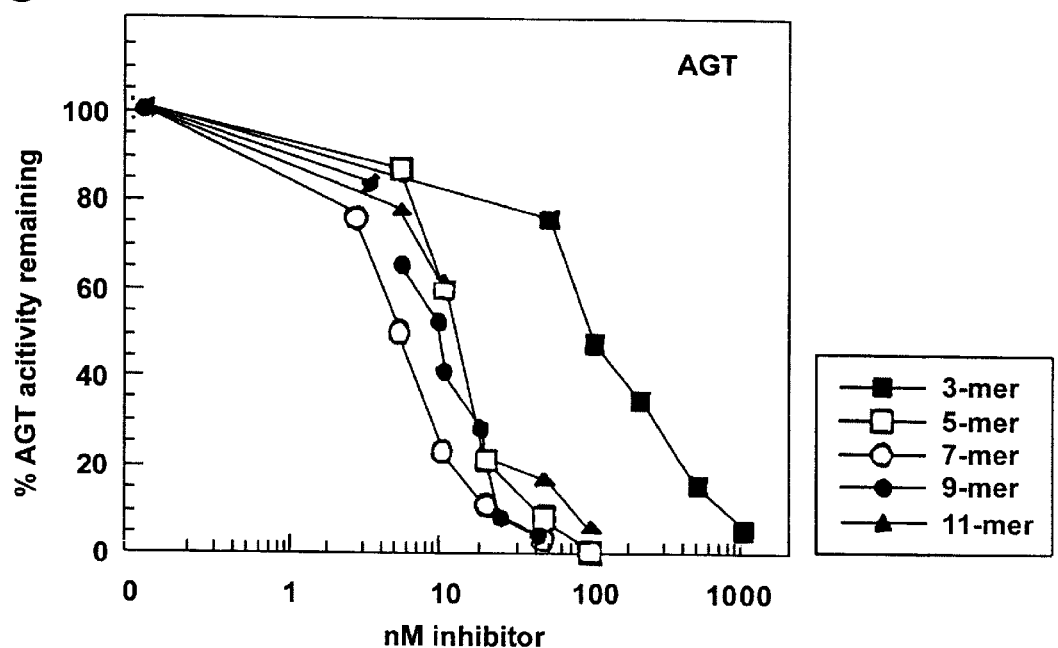
FIGS. 1A–C are graphs of percent remaining alkyltransferase activity (% AGT activity remaining) versus concentration of a single-stranded oligodeoxyribonucleotide (3–11 nts in length, designated 3-mer, 5-mer, 7-mer, 9-mer and 11-mer) comprising $O^6$-benzylguanine (nM Inhibitor) for wild-type human alkyltransferase (AGT, FIG. 1A) and mutant human alkyltransferases (G156A, FIG. 1B, and P140A, FIG. 1C).
Figure 1B:
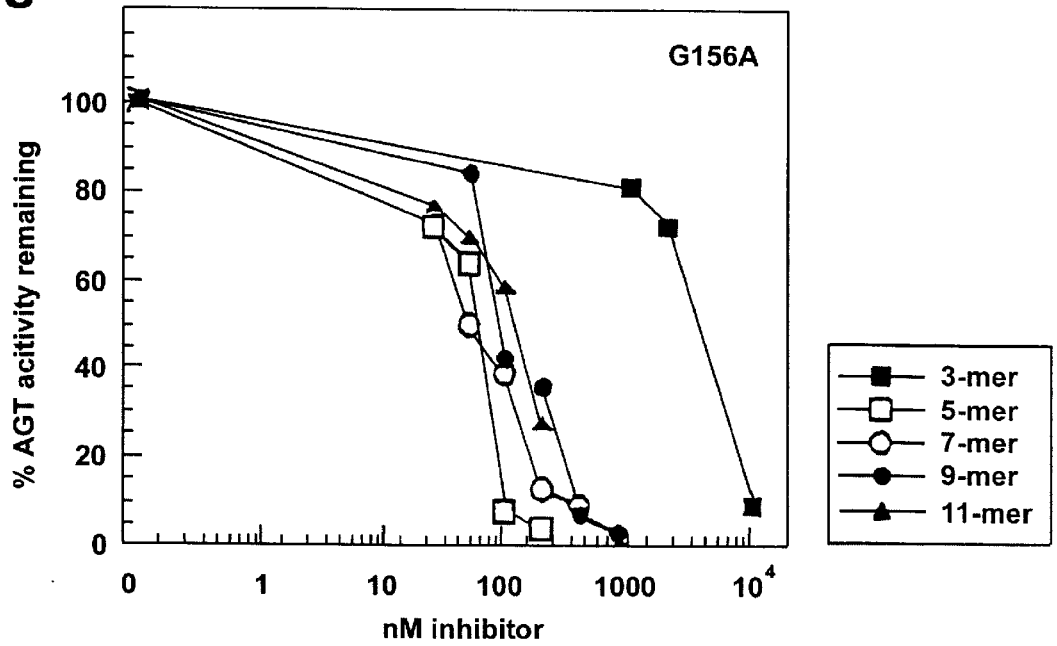
Figure 1C:
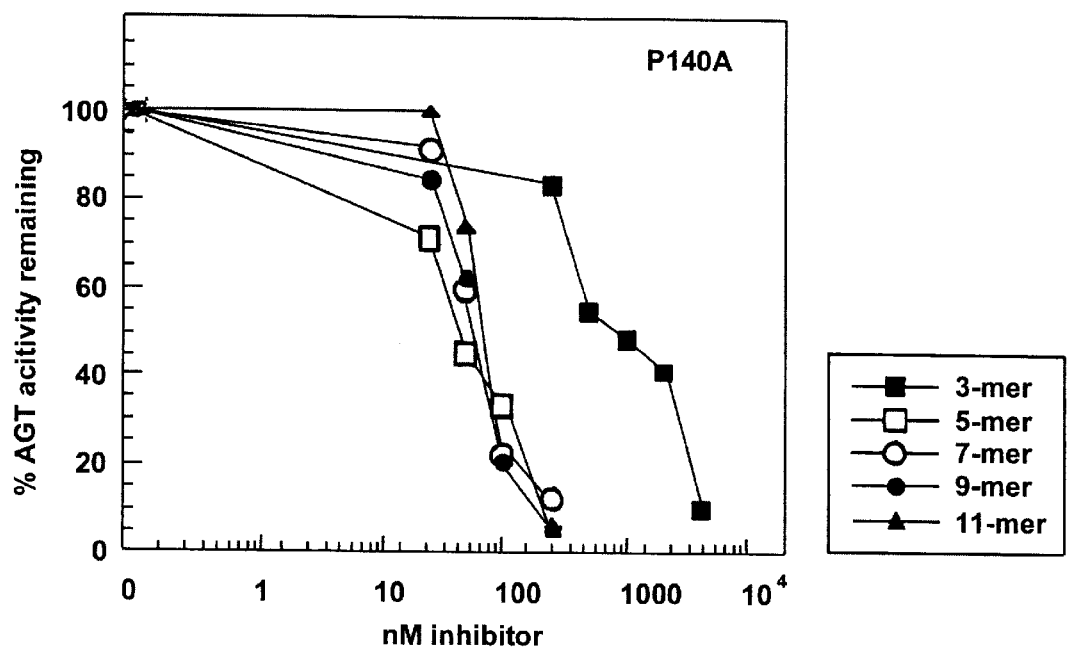

The present invention is predicated on the discovery that a single-stranded oligodeoxyribonucleotide, which comprises from about 5 to 11 bases, at least one of which is a substituted or an unsubstituted $O^6$-benzylguanine, is a more effective inactivator of human AGT than the free base $O^6$-benzylguanine. Not only is the single-stranded oligodeoxyribonucleotide more effective in inactivating human AGT, it does not suffer from the major disadvantage attendant the free base $O^6$-benzylguanine, namely its limited solubility in water. Another characteristic that distinguishes the single-stranded oligodeoxyribonucleotide from the free base $O^6$-benzylguanine is its ability to inactivate mutant human AGTs, which could be produced by various chemotherapeutic drugs, such as chloroethylating or methylating agents, in vivo and which either are not inactivated by $O^6$-benzylguanine or are less inactivated by $O^6$-benzylguanine than by the single-stranded oligodeoxyribonucleotide. In addition, the present inventive single-stranded oligodeoxyribonucleotides have been designed so that they are no longer than necessary to fit the active site of the human AGT, thereby rendering them easier to synthesize and purify than comparatively longer single-stranded oligodeoxyribonucleotides and double-stranded oligodeoxyribonucleotides.

In view of the above, the present invention provides a single-stranded oligodeoxyribonucleotide, which (i) comprises from about 5 to 11 bases, at least one of which is a substituted or an unsubstituted $O^6$-benzylguanine, and (ii) inactivates human AGT. Preferably, the single-stranded oligodeoxyribonucleotide comprises from about 7 to 11 bases, more preferably from about 9 to 11 bases. Examples of such oligodeoxyribonucleotides are set forth in Table I.

Although it is only necessary that a single base in the single-stranded oligodeoxyribonucleotide be a substituted or an unsubstituted $O^6$-benzylguanine, as many as two, three, four or even every base in the single-stranded oligodeoxyribonucleotide can be a substituted or an unsubstituted $O^6$-benzylguanine. If there is more than one substituted or unsubstituted $O^6$-benzylguanine present in the single-stranded oligodeoxyribonucleotide, they can be the same or different. A preferred single-stranded oligodeoxyribonucleotide is one in which the middle base is a substituted or an unsubstituted $O^6$-benzylguanine.

Although the at least one $O^6$-benzylguanine is preferably unsubstituted, the $O^6$-benzylguanine can be substituted. The manner in which the $O^6$-benzylguanine is substituted and the extent to which the $O^6$-benzylguanine is substituted is not narrowly critical to the practice of the present invention. All that matters is that the resulting single-stranded oligodeoxyribonucleotide inhibits human AGT.

Desirably, the single-stranded oligodeoxyribonucleotide inactivates human AGT more effectively than the free base $O^6$-benzylguanine. Preferably, the single-stranded oligodeoxyribonucleotide inactivates a mutant human AGT, which could be produced by various chemotherapeutic drugs, such as chloroethylating or methylating agents, in vivo and which either is not inactivated by $O^6$-benzylguanine or is less inactivated by $O^6$-benzylguanine than by the single-stranded oligodeoxyribonucleotide.

If the $O^6$-benzylguanine is substituted, preferably it is substituted with from one to five substituents, which can be the same or different and are hydro, halo, haloalkyl, hydroxy, hydroxyamino, hydrazino, an alkyl, an aryl, nitro, a polycyclic aromatic alkyl, a cycloalkyl, an alkenyl, an alkynyl, a hydroxyalkyl, an alkoxy, an alkoxylalkyl, an aryloxy, an acyloxy, an acyloxyalkyl, a monoalkylamino, a dialkylamino, an acylamino, an ureido, a thioureido, a carboxy, a carboxyalkyl, a cyano, a cyanoalkyl, C-formyl, C-acyl, a dialkoxyalkyl, or $SO_nR_1$, wherein n is an integer from zero to three and $R_1$ is hydro, a $C_1$–$C_6$ alkyl, or a $C_1$–$C_4$ alkyl-substituted or an unsubstituted aryl. The one to five substituents are independently substituted or unsubstituted. More preferably, the haloalkyl is a $C_2$–$C_6$ straight-chain or a $C_3$–$C_6$ branched-chain alkyl, which is substituted with from one to three halo groups, the alkyl is a $C_2$–$C_6$ straight-chain or a $C_3$–$C_6$ branched-chain alkyl, the aryl is substituted with a $C_1$–$C_8$ straight-chain or a $C_3$–$C_8$ branched-chain alkyl, the polycyclic aromatic alkyl comprises from two to four aromatic rings and a $C_{1-C6}$ straight-chain or a $C_3$–$C_6$ branched-chain alkyl, the cycloalkyl is a $C_3$–$C_8$ cycloalkyl, the alkenyl is a $C_2$–$C_6$ straight-chain or a $C_4$–$C_6$ branched-chain alkenyl, the alkynyl is a $C_2$–$C_6$ straight-chain or a $C_4$–$C_6$ branched-chain alkynyl, the hydroxyalkyl is a $C_{1-C6}$ straight-chain or a $C_3$–$C_6$ branched-chain hydroxyalkyl, the alkoxy is a $C_1$–$C_8$ straight-chain or a $C_3$–$C_8$ branched-chain alkoxy, the alkoxyalkyl is a $C_2$–$C_8$ alkoxyalkyl, the acyloxyalkyl comprises a $C_1$–$C_6$ straight-chain or a $C_3$–$C_6$ branched-chain alkyl, the monoalkylamino and the dialkylamino comprise a $C_1$–$C_6$ straight-chain or a $C_3$–$C_6$ branched-chain alkyl, the carboxyalkyl comprises a $C_1$–$C_6$ straight-chain or a $C_3$–$C_6$ branched-chain alkyl, the cyanoalkyl comprises a $C_1$–$C_6$ straight-chain or a $C_3$–$C_6$ branched-chain alkyl, and the dialkoxyalkyl comprises a $C_1$–$C_6$ straight-chain or a $C_3$–$C_6$ branched-chain alkoxy, which can be the same or different, and a $C_1$–$C_6$ straight-chain or a $C_3$–$C_6$ branched-cha $O^6$-benzylguanine can be prepared in accordance with the method set forth in Bowles et al., *J. Med. Chem.* 6: 471–480 (1963), or Frihart et al., *J. Am. Chem. Soc.* 95: 7144–7175 (1973). Substituted $O^6$-benzylguanines can be synthesized by reacting 2-amino-6-chloropurine with the alkoxide of a benzyl alcohol comprising a desired ortho, meta orpara substituent. Procedures that can be used to prepare substituted $O^6$-benzylguanine are set forth in Dolan et al. (1990), supra. Treatment of $O^6$-benzylguanine in its anionic form with alkylating agents, such as ethyl bromoacetate, 2-bromoacetamide, 1,2-epoxybutane, bromoacetonitrile or 1,3,4,6-tetra-O-acetyl-2-deoxy-2-(chloroacetamido)-β-D-glucose, are described in Moschel et al. (1992), supra, and Fondy et al., *J. Med Chem.* 21: 1222–1225 (1978). α-amino acid adducts of $O^6$-benzylguanine can be prepared by nucleophilic displacement by $O^6$-benzylguanine or its anion on selected reagents, such as the protected β-lactone of L-serine (Pansare et al., *Org. Syn.* 70: 1–9 (1991)) or (S)-3-amino-2-oxetanone (Pansare et al., *Org. Syn.* 70: 10–17 (1991)). Specific examples of synthesis of substituted $O^6$-benzylguanine are set forth in Moschel et al., U.S. Pat. No. 5,691,307.

Single-stranded oligodeoxyribonucleotides comprising at least one $O^6$-benzylguanine can be synthesized in accordance with methods known to those of ordinary skill in the art. For example, automated DNA synthetic procedures can be used to introduce a suitably protected phosphoramidite of $O^6$-benzyl-2'-deoxyguanosine into a DNA sequence at any location (Pauly et al. (1988), supra; and Pauly et al. (1991), supra). If desired, $O^6$-benzylguanine can be attached through a linker to a hydroxyl group at a terminal carbohydrate residue of an oligodeoxyribonucleotide, for example, by reacting 2-amino-6-benzyloxy-9-carboethoxymethylpurine with the hydroxyl group of the terminal carbohydrate residue of the oligodeoxyribonucleotide.

The above-described single-stranded oligodeoxyribonucleotide can be modified, for example, to increase its resistance to nuclease digestion in vivo. In this regard, at least one, although it can be more, phosphate is modified, preferably by replacement with a methylphosphonate or a phosphorothioate. More preferably, at least one of either of the terminal phosphates is replaced by a methylphosphonate or a phosphorothioate. Even more preferably, both of the terminal phosphates are independently replaced by a methylphosphonate or a phosphorothioate, i.e., the replacements can be the same or different. Such modifications are within the ordinary skill in the art (see, for example, Marcus-Sekura et al., *Nucleic Acids Research* 15: 5749–5763 (1987) and references cited therein). Care should be exercised to ensure that not so many phosphates in any given oligodeoxyribonucleotide are modified so as to affect adversely the ability of the oligodeoxyribonucleotide to inactivate human AGT.

Desirably, the single-stranded oligodeoxyribonucleotide also inactivates a mutant human alkyltransferase. Preferably, the mutant human alkyltransferase is one that either is not inactivated by $O^6$-benzylguanine or is less inactivated by $O^6$-benzylguanine than by the single-stranded oligodeoxyribonucleotide.

Whether or not a given single-stranded oligodeoxyribonucleotide inactivates a wild-type or mutant human alkyltransferase can be determined by measuring alkyltransferase depletion. For example, a stock solution (100 mM) of a given single-stranded oligodeoxyribonucleotide in an aqueous or mixed aqueous/organic solvent can be prepared. Solutions of the human wild-type AGT, mutant human AGT, or the AGT from HT29 cells and cell extracts (Domoradzki et al., *Carcinogenesis* 5: 1641–1647 (1984)) can be incubated with varying concentrations (between 0 and 400 μM, for example) of the oligodeoxyribonucleotide for 30 min in a buffer containing 50 mM Tris-HCl, pH 7.5, 0.1 mM EDTA, and 5 mM dithiothreitol, and alkyltransferase depletion can be measured. Alternatively, cells can be plated at a density of $5 \times 10^6$ cells/T75 flask and allowed to grow for three days, at which time the medium can be replaced with medium containing a given concentration of an oligodeoxyribonucleotide. After four hours, cells can be harvested and frozen at −80° C. for analysis of alkyltransferase depletion later. Alkyltransferase depletion is determined by measuring loss of $O^6$-[$^3$H]methylguanine, for example, from a [$^3$H] methylated DNA substrate, for example, which can be prepared by reacting [$^3$H]methylnitrosourea (21.5 Ci/mmol) with calf thymus DNA as described previously (Domoradzki et al. (1984), supra; and Dolan et al. (1990), supra).

Any oligodeoxyribonucleotide in accordance with the present invention that effectively depletes tumor cells of alkyltransferase activity as measured, for example, in the above-described assay, is expected to enhance the effect of an antineoplastic alkylating agent, which alkylates the $O^6$ the position of guanine residues in DNA, in the chemotherapeutic treatment of cancer in a mammal. This has been shown to be true with the weak alkyltransferase depleter $O^6$-benzylguaninemethylguanine (Dolan et al., *Cancer Research* 46: 4500–4504 (1986)) and the more potent alkyltransferase depleters $O^6$-benzylguanine and $O^6$-(p-chlorobenzyl)-and $O^6$-(p-methylbenzyl)-guanine (Dolan et al. (1990), supra; Dolan et al. (1991), supra; Dolan et al. (1993), supra; Mitchell et al., *Cancer Research* 52: 1171–1175 (1992); and Moschel et al., U.S. Pat. No. 5,691,307).

In addition to the above-described oligodeoxyribonucleotides, the present invention also provides a composition comprising a single-stranded oligodeoxyribonucleotide and a pharmaceutically acceptable carrier. Appropriate pharmaceutically acceptable carriers, vehicles, adjuvants, excipients and diluents are known in the art. The above-described oligodeoxyribonucleotides or pharmaceutically acceptable salts thereof can be formulated into solid, semi-solid, liquid or gaseous formulations. Examples of such formulations include tablets, capsules, powders, granules, ointments, solutions, suppositories, injections, inhalants and aerosols. The choice of formulation will be determined, in part, by the particular route of administration chosen. The following formulations are merely exemplary and are, in no way, limiting.

Compositions for oral administration (also, buccal or sublingual) can comprise additives, such as lactose, mannitol, corn starch or potato starch, binders, such as crystalline cellulose, cellulose derivatives, acacia, corn starch or gelatin, with sodium carboxymethylcellulose, lubricants, such as talc or magnesium stearate, and, if desired, diluents, buffering agents, moistening agents, preservatives and flavoring agents. Such compositions can be in the form of tablets, powders, granules or capsules, for example. Unit dosage forms for oral administration, such as syrups, elixirs and suspensions, wherein each dosage unit, e.g., teaspoonful or tablespoonful, contains a predetermined amount of a present inventive oligodeoxyribonucleotide, can be combined with sterile water for injection (USP) or normal saline.

Compositions for administration in the form of suppositories can comprise a base. Suitable bases include emulsifying bases and water-soluble bases. Vehicles, such as cocoa butter, carbowaxes and polyethylene glycols, which are solid at room temperature and melt at body temperature, also can be used.

Compositions for transdermal administration comprise an appropriate vehicle or salt. Adsorption can be aided by the use of an electric current or field.

Compositions for administration by injection can be prepared by dissolving, suspending or emulsifying a present inventive oligodeoxyribonucleotide in an aqueous or non-aqueous solvent, such as vegetable oil, synthetic aliphatic acid glycerides, esters of higher aliphatic acids or propylene glycol. Solubilizers, isotonic agents, suspending agents, emulsifying agents, stabilizers and preservatives can be added, if desired.

Compositions for aerosolized administration can be prepared in the form of a liquid or minute powder. An aerosol container can be filled with gaseous or liquid spraying agents and, if desired, conventional adjuvants, such as humidifying agents. Suitable propellants include dichlorodifluoromethane, propane, nitrogen and the like. If desired, the composition can be formulated for non-pressurized preparations, such as a nebulizer or an atomizer.

In view of the above, the present invention also provides a method of enhancing the effect of an antineoplastic alkylating agent, which alkylates the $O^6$ position of guanine residues in DNA, in the chemotherapeutic treatment of cancer in a mammal, particularly a human. The method comprises co-administering to the mammal a cancer-treatment effective amount of an antineoplastic alkylating agent and a chemotherapeutic treatment-enhancing amount of a single-stranded oligodeoxyribonucleotide in accordance with the present invention.

By "enhancing the effect of an antineoplastic alkylating agent" is meant that the antineoplastic alkylating agent has a greater effect in the presence of a present inventive oligodeoxyribonucleotide than in the absence of a present inventive oligodeoxyribonucleotide. When an alkyltransferase acts on the oligodeoxyribonucleotide, it is inactivated and, therefore, is not able to act on the DNA in a cancerous cell that has been alkylated by the antineoplastic alkylating agent. Given that the alkyltransferase is not able to act on the alkylated DNA in a cancerous cell, the DNA in the cancerous cell is not repaired, thereby leading to death of the cancerous cell.

By "coadministering" is meant administering the antineoplastic alkylating agent and the oligodeoxyribonucleotide sufficiently close in time such that the oligodeoxyribonucleotide can enhance the effect of the antineoplastic alkylating agent. In this regard, the oligodeoxyribonucleotide can be administered first and the antineoplastic alkylating agent can be administered second or vice versa. Alternatively, the oligodeoxyribonucleotide and the antineoplastic alkylating agent can be administered simultaneously. In addition, a combination of oligodeoxyribonucleotides can be administered, and one or more oligodeoxyribonucleotides can be administered in combination with another agent useful in the treatment of cancer.

By "cancer-treatment effective amount of an antineoplastic alkylating agent" is meant that the antineoplastic alkylating agent is administered in a dose sufficient to treat the cancer. Such doses are known in the art (see, for example, the *Physicians' Desk Reference*). For example, 1,3-bis(2-chloroethyl)-1-nitrosourea (carmustine or BCNU, Bristol-Myers, Evansville, Ind.) can be administered intravenously at a dosage of from about 150 to 200 mg/m$^2$ every six weeks. Another alkylating agent, namely 1-(2-chloroethyl)-3-cyclohexyl-1-nitrosourea (lomustine or CCNU, Bristol-Myers), can be administered orally at a dosage of about 130 mg/m$^2$ every six weeks. By "chemotherapeutic treatment-enhancing amount of a single-stranded oligodeoxyribonucleotide" is meant that the oligodeoxyribonucleotide is administered in a dose sufficient to enhance the effect of the antineoplastic alkylating agent. A suitable dosage is that which will result in a concentration of oligodeoxyribonucleotide in the cancerous cells to be treated sufficient to deplete alkyltransferase activity, e.g., from about 10 nM to 200 nM intracellularly, which may require an extracellular concentration of from about 10 $\mu$M to 50 $\mu$M. The dose can be adjusted as necessary to enhance the effect of the antineoplastic alkylating agent.

The present inventive oligodeoxyribonucleotides are useful in enhancing the effect of any antineoplastic alkylating agent, provided that the agent is one that alkylates the $O^6$ position of guanine residues in DNA. Examples of antineoplastic alkylating agents include chloroethylating agents. The most frequently used chloroethylating agents include 1-(2-chloroethyl)-3-cyclohexyl-1-nitrosourea (CCNU, lomustine), 1,3-bis(2-chloroethyl)-1-nitrosourea (BCNU, carmustine), 1-(2-chloroethyl)-3-(4-methylcyclohexyl)-1-nitrosourea (MeCCNU, semustine), and 1-(2-chloroethyl)-3-(4-amino-2-methyl-5-pyrimidinyl)methyl-1-nitrosourea (ACNU). Such agents have been used clinically against tumors of the central nervous system, multiple myeloma, melanoma, lymphoma, gastrointestinal tumors, and other solid tumors (Colvin and Chabner. Alkylating Agents. In: *Cancer Chemotherapy: Principles and Practice*. Edited by B. A. Chabner and J. M. Collins, Lippincott, Philadelphia, Pa. pp. 276–313 (1990); and McCormick et al., *Eur. J. Cancer* 26: 207–221 (1990)). Chloroethylating agents, which have fewer side effects and are currently under development include 1-(2-chloroethyl)-3-(2-hydroxyethyl)-1-nitrosourea (HECNU), 2-chloroethylmethylsulfonylmethanesulfonate (Clomesone), and 1-[N-(2-chloroethyl)-N-nitrosoureido] ethylphosphonic acid diethyl ester (Fotemustine) (Colvin and Chabner (1990), supra; and McCormick et al. (1990), supra). Methylating agents include Streptozotocin (2-deoxy-2-(3-methyl-3-nitrosoureido)-D-glucopyranose), Procarbazine (N-(1-methylethyl)-4-[(2-methylhydrazino)methyl] benzamide), Dacarbazine or DTIC (5-(3,3-dimethyl-1-triazenyl)-1H-imidazole-4-carboxamide), and Temozolomide (8-carbamoyl-3-methylimidazo[5.1-d]-1,2,3,5-tetrazin-4-(3H)-one).

Temozolomide is active against malignant melanomas, brain tumors and mycosis fungoides. Streptozotocin is effective against pancreatic tumors. Procarbazine is used to treat Hodgkin's disease and brain tumors. DTIC is used to treat melanoma and lymphomas (Colvin and Chabner (1990), supra; and Longo, *Semin. Concol.* 17: 716–735 (1990)).

The antineoplastic alkylating agent can be administered by any route. Conventional means of administration are described in Wasserman et al. (*Cancer* 36: 1258–1268 (1975)) and in the *Physicians' Desk Reference* (44$^{th}$ ed., Edward R. Barnhart, publisher, 1990.).

The present inventive method can be used to treat any cancer susceptible to treatment by an antineoplastic alkylating agent. Examples of such cancers include prostate cancer, brain cancer, lymphoma, leukemia, breast cancer, ovarian cancer, lung cancer, Wilms' tumor, rhabdomyosarcoma, multiple myeloma, stomach cancer, soft-tissue sarcoma, Hodgkin's disease, and non-Hodgkin's lymphoma.

The following example further illustrates the present invention. The example, of course, should not be construed as in any way limiting the scope of the present invention.

$O^6$-benzylguanine was synthesized as previously described (Dolan et al. (1990), supra). Single-stranded oligodeoxyribonucleotides also were synthesized in accordance with methods described by Pauly et al. (1991), supra.

$O^6$-benzylguanine was purified by crystallization from water and the oligodeoxyribonucleotides were purified by HPLC (Pauly et al. (1988), supra). The composition of the oligodeoxyribonucleotides was confirmed by enzymatic digestion to 2'-deoxyribonucleosides (Pauly et al. (1988), supra).

EXAMPLE

This example demonstrates that wild-type and mutant human alkyltransferases are more sensitive to inactivation by a single-stranded oligodeoxyribonucleotide comprising $O^6$-benzylguanine than by $O^6$-benzylguanine, itself.

Wild-type human AGT and mutants thereof, namely P140A and G156A, were prepared using the pIN vector expression system. pIN-AGT, pIN-P140A (Pro-140 to Ala) and pIN-G156A (Gly-156 to Ala) (Crone et al. (1993), supra; Crone et al. (1994), supra; and Pegg et al. (1993), supra).

The wild-type and mutant AGT proteins expressed from the pIN vectors were purified to homogeneity by ammonium sulfate precipitation, Mono-S chromatography and gel filtration as previously described (Pegg et al. (1993), supra; and Kanugula et al. (1995), supra). The purified protein was then incubated with $O^6$-benzylguanine, $O^6$-benzyl-2'-deoxyguanosine, or a single-stranded oligodeoxyribonucleotide ranging in length from three to eleven bases and comprising $O^6$-benzylguanine in 0.1 ml of 50 mM Tris-HCl, pH 7.5, 0.1 mM EDTA and 5.0 mM dithiothreitol for 30 min at 37° C. Afterwards, residual AGT activity was determined by a 30 min incubation with a [$^3$H]-methylated DNA substrate (1.0 ml volume), which had been methylated by reaction with N-[$^3$H]-methyl-N-nitrosourea as previously described (Dolan et al. (1993), supra; and Dolan et al. (1991), supra).

The results were expressed as the percentage of the AGT activity remaining and then used to calculate the $ED_{50}$ value (the concentration needed to reduce AGT activity by 50%) for the inactivator as shown in Table I.

TABLE I

| | $ED_{50}$ for inactivation of AGT (nM) | | |
|---|---|---|---|
| Oligodeoxyribonucleotide | AGT | G156A | P140A |
| $O^6$-benzylguanine[a] | 200 | 60,000 | 5,000 |
| $O^6$-benzyl-2'-deoxyguanosine[b] | 2000 | >100,000 | >20,000 |
| 5'-d(Ab$^6$GC)-3' | 90 | 4600 | 770 |
| 5'-d(GAb$^6$GCT)-3' | 13 | 60 | 50 |
| 5'-d(TGAb$^6$GCTG)-3' | 7 | 50 | 60 |
| 5'-d(GTGAb$^6$GCTGT)-3' | 8 | 90 | 60 |
| 5'-d(TGTGAb$^6$GCTGTG)-3' | 13 | 110 | 75 |

[a]Data previously published (Crone et al. (1993), supra; and Crone et al. (1994), supra).
[b]Data previously published (Moschel et al. (1992), supra).

The results demonstrate that a single-stranded oligodeoxyribonucleotide comprising $O^6$-benzylguanine (b$^6$G), even one as short as three nucleotides, was more effective in inactivating wild-type and mutant AGTs than the free base $O^6$-benzylguanine or $O^6$-benzyl-2'-deoxyguanosine. In this regard, oligodeoxyribonucleotides, which were from 5 to 11 nucleotides in length and which comprised $O^6$-benzylguanine, inactivated the mutant AGTs P140A and G156A at 4-fold and 11-fold higher concentrations, respectively, than the concentration required to inactivate wild-type AGT, whereas $O^6$-benzylguanine inactivated the mutant AGTs P140A and G156A at 25-fold and 300-fold higher concentrations, respectively, than the concentration required to inactivate wild-type AGT. Maximal effectiveness was observed for oligodeoxyribonucleotides that were from about 5 to about 11 nucleotides in length. There was no significant loss (<5%) of AGT activity in the absence of inactivator.

All of the references cited herein, whether patents, patent applications or publications, are hereby incorporated in their entireties by reference.

While this invention has been described with an emphasis upon preferred embodiments, it will be obvious to those of ordinary skill in the art that variations of the preferred embodiments can be used and that it is intended that the invention can be practiced otherwise than as specifically described herein. Accordingly, this invention includes all modifications encompassed within the spirit and scope of the invention as defined by the following claims.

What is claimed is:

1. A single-stranded oligodeoxyribonucleotide of not less than 5 and not more than 11 bases in length comprising at least one substituted or unsubstituted $O^6$-benzylguanine, wherein said single-stranded oligodeoxyribonucleotide inactivates human alkyltransferase.

2. The single-stranded oligodeoxyribonucleotide of claim 1, wherein said oligodeoxyribonucleotide is of not less than 7 bases in length.

3. The single-stranded oligodeoxyribonucleotide of claim 2, wherein said oligodeoxyribonucleotide is of not less than 9 bases in length.

4. The single-stranded oligodeoxyribonucleotide of claim 1, wherein said $O^6$-benzylguanine is substituted with from one to five substituents, which can be the same or different and are selected from the group consisting of hydro, halo, haloalkyl, hydroxy, hydroxyamino, hydrazino, an alkyl, an aryl, nitro, a polycyclic aromatic alkyl, a cycloalkyl, an alkenyl, an alkynyl, a hydroxyalkyl, an alkoxy, an alkoxyalkyl, an aryloxy, an acyloxy, an acyloxyalkyl, a monoalkylamino, a dialkylamino, an acylamino, a ureido, a thioureido, a carboxy, a carboxyalkyl, a cyano, a cyanoalkyl, C-formyl, C-acyl, a dialkoxyalkyl, and $SO_nR_1$, wherein n is an integer from zero to three and $R_1$ is hydro, a $C_1$–$C_6$ alkyl, or a $C_1$–$C_4$ alkyl-substituted or an unsubstituted aryl.

5. The single-stranded oligodeoxyribonucleotide of claim 4, wherein said from one to five substituents are further substituted.

6. The single-stranded oligodeoxyribonucleotide of claim 4, wherein said haloalkyl is a $C_2$–$C_6$ straight-chain or a $C_3$–$C_6$ branched-chain alkyl, which is substituted with from one to three halo groups, said alkyl is a $C_2$–$C_6$ straight-chain or a $C_3$–$C_6$ branched-chain alkyl, said aryl is substituted with a $C_1$–$C_8$ straight-chain or a $C_3$–$C_8$ branched-chain alkyl, said polycyclic aromatic alkyl comprises from two to four aromatic rings and a $C_1$–$C_6$ straight-chain or a $C_3$–$C_6$ branched-chain alkyl, said cycloalkyl is a $C_3$–$C_8$ cycloalkyl, said alkenyl is a $C_2$–$C_6$ straight-chain or a $C_4$–$C_6$ branched-chain alkenyl, said alkynyl is a $C_2$–$C_6$ straight-chain or a $C_4$–$C_6$ branched-chain alkynyl, said hydroxyalkyl is a $C_1$–$C_6$ straight-chain or a $C_3$–$C_6$ branched-chain hydroxyalkyl, said alkoxy is a $C_1$–$C_8$ straight-chain or a $C_3$–$C_8$ branched-chain alkoxy, said alkoxyalkyl is a $C_2$–$C_8$ alkoxyalkyl, said acyloxyalkyl comprises a $C_1$–$C_6$ straight-chain or a $C_3$–$C_6$ branched-chain alkyl, said monoalkylamino and said dialkylamino comprise a $C_1$–$C_6$ straight-chain or a $C_3$–$C_6$ branched-chain alkyl, said carboxyalkyl comprises a $C_1$–$C_6$ straight-chain or a $C_3$–$C_6$ branched-chain alkyl, said cyanoalkyl comprises a $C_1$–$C_6$ straight-chain or a $C_3$–$C_6$ branched-chain alkyl, and said dialkoxyalkyl comprises a $C_1$–$C_6$ straight-chain or a $C_3$–$C_6$ branched-chain alkoxy, which can be the same or different, and a $C_1$–$C_6$ straight-chain or a $C_3$–$C_6$ branched-chain alkyl.

7. The single-stranded oligodeoxyribonucleotide of claim 1, wherein said at least one substituted or unsubstituted $O^6$-benzylguanine is flanked by an equal number of bases in the 3'-direction as in the 5'-direction.

8. The single-stranded oligodeoxyribonucleotide of claim 1, in which at least one phosphate is modified.

9. The single-stranded oligodeoxyribonucleotide of claim 8, wherein said at least one phosphate is replaced by a methylphosphonate or a phosphorothioate.

10. The single-stranded oligodeoxyribonucleotide of claim 8, wherein said at least one phosphate is a terminal internucleoside phosphate.

11. The single-stranded oligodeoxyribonucleotide of claim 10, wherein two terminal internucleoside phosphates are independently replaced.

12. The single-stranded oligodeoxyribonucleotide of claim 1, which also inhibits a mutant human alkyltransferase, which either is not inactivated by $O_6$-benzylguanine or is less inactivated by $O^6$-benzylguanine than by said single-stranded oligodeoxyribonucleotide.

13. The single-stranded oligodeoxyribonucleotide of claim 1, wherein said oligodeoxyribonucleotide is selected from the group consisting of 5'-d (GAb$^6$GCT)-3', 5'-d (TGAb$^6$GCTG)-3', 5'-d (GTGAb$^6$GCTGT)-3', and 5'-d (TGTGAb$^6$GCTGTG)-3'. [SEQ ID NO: 1].

14. A composition comprising the single-stranded oligodeoxyribonucleotide of claim 1 and a pharmaceutically acceptable carrier.

15. A composition comprising the single-stranded oligodeoxyribonucleotide of claim 2 and a pharmaceutically acceptable carrier.

16. A composition comprising the single-stranded oligodeoxyribonucleotide of claim 3 and a pharmaceutically acceptable carrier.

17. A composition comprising the single-stranded oligodeoxyribonucleotide of claim 4 and a pharmaceutically acceptable carrier.

18. A composition comprising the single-stranded oligodeoxyribonucleotide of claim 5 and a pharmaceutically acceptable carrier.

19. A composition comprising the single-stranded oligodeoxyribonucleotide of claim 6 and a pharmaceutically acceptable carrier.

20. A composition comprising the single-stranded oligodeoxyribonucleotide of claim 7 and a pharmaceutically acceptable carrier.

21. A composition comprising the single-stranded oligodeoxyribonucleotide of claim 8 and a pharmaceutically acceptable carrier.

22. A composition comprising the single-stranded oligodeoxyribonucleotide of claim 9 and a pharmaceutically acceptable carrier.

23. A composition comprising the single-stranded oligodeoxyribonucleotide of claim 10 and a pharmaceutically acceptable carrier.

24. A composition comprising the single-stranded oligodeoxyribonucleotide of claim 11 and a pharmaceutically acceptable carrier.

25. A composition comprising the single-stranded oligodeoxyribonucleotide of claim 12 and a pharmaceutically acceptable carrier.

26. A composition comprising the single-stranded oligodeoxyribonucleotide of claim 13 and a pharmaceutically acceptable carrier.

27. A method of enhancing the effect of an antineoplastic alkylating agent, which alkylates the $O^6$ position of guanine residues in DNA, in the chemotherapeutic treatment of cancer in a mammal, which method comprises co-administering to the mammal a cancer-treatment effective amount of an antineoplastic alkylating agent and a chemotherapeutic treatment-enhancing amount of a single-stranded oligodeoxyribonucleotide of claim 1.

28. A method of enhancing the effect of an antineoplastic alkylating agent, which alkylates the $O^6$ position of guanine residues in DNA, in the chemotherapeutic treatment of cancer in a mammal, which method comprises co-administering to the mammal a cancer-treatment effective amount of an antineoplastic alkylating agent and a chemotherapeutic treatment-enhancing amount of a single-stranded oligodeoxyribonucleotide of claim 2.

29. A method of enhancing the effect of an antineoplastic alkylating agent, which alkylates the $O^6$ position of guanine residues in DNA, in the chemotherapeutic treatment of cancer in a mammal, which method comprises co-administering to the mammal a cancer-treatment effective amount of an antineoplastic alkylating agent and a chemotherapeutic treatment-enhancing amount of a single-stranded oligodeoxyribonucleotide of claim 3.

30. A method of enhancing the effect of an antineoplastic alkylating agent, which alkylates the $O^6$ position of guanine residues in DNA, in the chemotherapeutic treatment of cancer in a mammal, which method comprises co-administering to the mammal a cancer-treatment effective amount of an antineoplastic alkylating agent and a chemotherapeutic treatment-enhancing amount of a single-stranded oligodeoxyribonucleotide of claim 4.

31. A method of enhancing the effect of an antineoplastic alkylating agent, which alkylates the $O^6$ position of guanine residues in DNA, in the chemotherapeutic treatment of cancer in a mammal, which method comprises co-administering to the mammal a cancer-treatment effective amount of an antineoplastic alkylating agent and a chemotherapeutic treatment-enhancing amount of a single-stranded oligodeoxyribonucleotide of claim 5.

32. A method of enhancing the effect of an antineoplastic alkylating agent, which alkylates the $O^6$ position of guanine residues in DNA, in the chemotherapeutic treatment of cancer in a mammal, which method comprises co-administering to the mammal a cancer-treatment effective amount of an antineoplastic alkylating agent and a chemotherapeutic treatment-enhancing amount of a single-stranded oligodeoxyribonucleotide of claim 6.

33. A method of enhancing the effect of an antineoplastic alkylating agent, which alkylates the $O^6$ position of guanine residues in DNA, in the chemotherapeutic treatment of cancer in a mammal, which method comprises co-administering to the mammal a cancer-treatment effective amount of an antineoplastic alkylating agent and a chemotherapeutic treatment-enhancing amount of a single-stranded oligodeoxyribonucleotide of claim 7.

34. A method of enhancing the effect of an antineoplastic alkylating agent, which alkylates the $O^6$ position of guanine residues in DNA, in the chemotherapeutic treatment of cancer in a mammal, which method comprises co-administering to the mammal a cancer-treatment effective amount of an antineoplastic alkylating agent and a chemotherapeutic treatment-enhancing amount of a single-stranded oligodeoxyribonucleotide of claim 8.

35. A method of enhancing the effect of an antineoplastic alkylating agent, which alkylates the $O^6$ position of guanine residues in DNA, in the chemotherapeutic treatment of cancer in a mammal, which method comprises co-administering to the mammal a cancer-treatment effective amount of an antineoplastic alkylating agent and a chemotherapeutic treatment-enhancing amount of a single-stranded oligodeoxyribonucleotide of claim 9.

36. A method of enhancing the effect of an antineoplastic alkylating agent, which alkylates the $O^6$ position of guanine residues in DNA, in the chemotherapeutic treatment of cancer in a mammal, which method comprises co-administering to the mammal a cancer-treatment effective amount of an antineoplastic alkylating agent and a chemotherapeutic treatment-enhancing amount of a single-stranded oligodeoxyribonucleotide of claim 10.

37. A method of enhancing the effect of an antineoplastic alkylating agent, which alkylates the $O^6$ position of guanine residues in DNA, in the chemotherapeutic treatment of cancer in a mammal, which method comprises co-administering to the mammal a cancer-treatment effective amount of an antineoplastic alkylating agent and a chemotherapeutic treatment-enhancing amount of a single-stranded oligodeoxyribonucleotide of claim 11.

38. A method of enhancing the effect of an antineoplastic alkylating agent, which alkylates the $O^6$ position of guanine residues in DNA, in the chemotherapeutic treatment of cancer in a mammal, which method comprises co-administering to the mammal a cancer-treatment effective amount of an antineoplastic alkylating agent and a chemotherapeutic treatment-enhancing amount of a single-stranded oligodeoxyribonucleotide of claim 12.

39. A method of enhancing the effect of an antineoplastic alkylating agent, which alkylates the $O^6$ position of guanine residues in DNA, in the chemotherapeutic treatment of cancer in a mammal, which method comprises co-administering to the mammal a cancer-treatment effective amount of an antineoplastic alkylating agent and a chemotherapeutic treatment-enhancing amount of a single-stranded oligodeoxyribonucleotide of claim 13.

40. A single stranded oligodeoxyribonucleotide that inactivates human alkyltransferase comprising the sequence 5'-dGAb$^6$GCT-3' wherein b$^6$G is a substituted or unsubstituted $O^6$-benzylguanine.

41. A composition comprising the single-stranded oligodeoxyribonucleotide of claim 40 and a pharmaceutically acceptable carrier.

42. A method of enhancing the effect of an antineoplastic alkylating agent, which alkylates the $O^6$-position of guanine residues in DNA, in the chemotherapeutic treatment of cancer in a mammal, which method comprises co-administering to the mammal a cancer-treatment effective amount of an antineoplastic alkylating agent and a chemotherapeutic treatment-enhancing amount of a single-stranded oligodeoxyribonucleotide of claim 40.

43. A single stranded oligodeoxyribonucleotide that inactivates human alkyltransferase consisting of 5 to 11 bases at least one of which is a substituted or unsubstituted $O^6$-benzylguanine.

44. A composition comprising the single-stranded oligodeoxyribonucleotide of claim 43 and a pharmaceutically acceptable carrier.

45. A method of enhancing the effect of an antineoplastic alkylating agent, which alkylates the $O^6$-position of guanine residues in DNA, in the chemotherapeutic treatment of cancer in a mammal, which method comprises co-administering to the mammal a cancer-treatment effective amount of an antineoplastic alkylating agent and a chemotherapeutic treatment-enhancing amount of a single-stranded oligodeoxyripbonucleotide of claim 43.

46. A method of enhancing the effect of an antineoplastic alkylating agent, which alkylates the $O^6$-position of guanine residues in DNA, in the chemotherapeutic contacting of cancer cells in vitro, which method comprises co-administering to the cancer cells an antineoplastic alkylating agent and a single-stranded oligodeoxyribonucleotide of claim 1.

47. A single-stranded oligodeoxyribonucleotide of not less than 5 and not more than 11 substituted or unsubstituted bases in length comprising at least one substituted or unsubstituted $O^6$-benzylguanine base, and which inactivates human alkyltransferase.

48. The single-stranded oligodeoxyribonucleotide of claim 47, wherein at least one of the 5 to 11 bases other than the substituted or unsubstituted $O^6$-benzylguanine base is substituted.

49. The single-stranded oligodeoxyribonucleotide of claim 47, comprising at least one modified internucleoside phosphate linkage.

50. The single-stranded oligodeoxyribonucleotide of claim 49, comprising two or more modified internucleoside phosphate linkages.

51. The single-stranded oligodeoxyribonucleotide of claim 49, wherein said modified internucleoside phosphate linkage is a modified terminal internucleoside phosphate linkage.

52. The single-stranded oligodeoxyribonucleotide of claim 51, wherein said modified terminal internucleoside phosphate linkage is a methylphosphonate or a phosphorothioate.

53. A modified single-stranded oligodeoxyribonucleotide of not less than 5 and not more than 11 substituted or unsubstituted bases in length comprising at least one substituted or unsubstituted $O^6$-benzylguanine base, and which inactivates human alkyltransferase.

54. The single-stranded oligodeoxyribonucleotide of claim 1, including a plurality of substituted or unsubstituted $O^6$-benzylguanine bases.

55. The single-stranded oligodeoxyribonucleotide of claim 54, including at least three substituted or unsubstituted $O^6$-benzylguanine bases.

56. The single-stranded oligodeoxyribonucleotide of claim 54, including at least four substituted or unsubstituted $O^6$-benzylguanine bases.

57. The single-stranded oligodeoxyribonucleotide of claim 54, including at least five substituted or unsubstituted $O^6$-benzylguanine bases.

58. The single-stranded oligodeoxyribonucleotide of claim 2, including a plurality of substituted or unsubstituted $O^6$-benzylguanine bases.

59. The single-stranded oligodeoxyribonucleotide of claim 58, including at least three substituted or unsubstituted $O^6$-benzylguanine bases.

60. The single-stranded oligodeoxyribonucleotide of claim 58, including at least four substituted or unsubstituted $O^6$-benzylguanine bases.

61. The single-stranded oligodeoxyribonucleotide of claim 58, including at least five substituted or unsubstituted $O^6$-benzylguanine bases.

\* \* \* \* \*